United States Patent [19]

Hanisch et al.

[11] Patent Number: 4,462,940
[45] Date of Patent: Jul. 31, 1984

[54] PROCESS FOR THE RECOVERY OF HUMAN β-INTERFERON-LIKE POLYPEPTIDES

[75] Inventors: Wolfgang H. Hanisch, Oakland; Peter M. Fernandes, Lafayette, both of Calif.

[73] Assignee: Cetus Corporation, Emeryville, Calif.

[21] Appl. No.: 495,896

[22] Filed: May 18, 1983

Related U.S. Application Data

[63] Continuation-in-part of Ser. No. 422,421, Sep. 23, 1982, abandoned.

[51] Int. Cl.³ .................... C07G 7/00; A61K 45/02
[52] U.S. Cl. ........................ 260/112 R; 435/68; 435/811; 424/85
[58] Field of Search ............ 435/68, 811; 260/112 R; 424/85

[56] References Cited

U.S. PATENT DOCUMENTS

| | | | |
|---|---|---|---|
| 3,800,035 | 3/1974 | Goore | 435/811 X |
| 3,855,197 | 12/1974 | Hirsch et al. | 435/272 X |
| 4,278,661 | 7/1981 | Knight | 435/811 X |
| 4,289,689 | 9/1981 | Friesen et al. | 424/85 X |
| 4,289,850 | 9/1981 | Robinson | 435/811 X |
| 4,315,852 | 2/1982 | Leibowitz et al. | 260/112 R |
| 4,343,735 | 8/1982 | Menge et al. | 260/112 R |
| 4,343,736 | 8/1982 | Uemura et al. | 260/112 R |

OTHER PUBLICATIONS

Derynek et al., Expression of Human Fibroblast Interferon Gene in *E. coli*, *Nature*, 287, (1980), 193.
Scandella et al., A Membrane-Bound Phospholipase A1 Purified from *E. coli*, *Biochemistry*, 10(24), 1971, 4447.
U.S. Ser. No. 353,360 filed Mar. 1, 1982, entitled "Process for Recovering Human IFN-β from a Transformed Microorganism".

*Primary Examiner*—John Kight, III
*Assistant Examiner*—Garnette D. Draper
*Attorney, Agent, or Firm*—Albert P. Halluin; Janet E. Hasak; Shyamala T. Rajender

[57] ABSTRACT

An improved process for recovering and purifying β-HIFN from transformed bacterial comprising concentrating the bacteria; disrupting the cell wall and solubilizing the β-HIFN into an aqueous medium with an appropriate solubilizing agent; extracting the β-HIFN from the aqueous medium with 2-butanol, 2-methyl-2-butanol or mixtures thereof; precipitating and isolating the β-HIFN from the alcohol phase; purifying the β-HIFN by chromatography and diafiltering the β-HIFN against distilled water or aqueous solutions of ethanol or glycerol at a pH of about 12; and therapeutic formulations and compositions of β-HIFN within SDS levels therein reduced to less than 10 p.p.m.

32 Claims, 4 Drawing Figures

PROCESS FOR THE RECOVERY OF HUMAN β-INTERFERON-LIKE POLYPEPTIDES This application is a continuation-in-part of copending U.S. Ser. No. 422,421, filed Sept. 23, 1982 abandoned.

BACKGROUND OF THE INVENTION

This invention is in the general field of biochemical engineering. More specifically, the subject invention relates to the preparation of human interferons and interferon-like polypeptides. Still more specifically, the subject invention relates to an improved process for the production and recovery of human fibroblast interferon and interferon-like polypeptides (β-HIFN) from genetically transformed microorganisms, β-HIFN preparations of relatively high purity, and therapeutically acceptable formulations thereof.

This application is also related to U.S. Ser. No. 353,360, "Process For Recovering Human IFN-β From A Transformed Microorganism," filed March 1, 1982, and assigned to Cetus Corporation.

Naturally occurring interferons (IFNs) are species-specific proteins, often glycoproteins, produced by various cells upon induction with viruses, double stranded RNA's, other polynucleotides, antigens and mitogens. Interferons exhibit multiple biological activities such as antiviral, antiproliferative, immunomodulatory and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as $\alpha$, $\beta$ and $\gamma$ interferons. These are reported to be different proteins coded for by distinct structural genes.

Since their discovery in 1957, interferons have been extensively and intensively investigated for their potential therapeutic use as antiviral and/or anti-cancer agents. However, the paucity of adequate amounts of the material isolated from natural sources and the expense involved, have precluded extensive clinical testing and evaluation of the extent of the therapeutic value of these interferons.

In recent times, however, several of the human interferon genes have been cloned using recombinant DNA technology and expressed in *E. coli* (Nagola, S. et al., *Nature* 284: 316 (1980); Goeddel, D. V. et al., *Nature*, 287: 411 (1980); Yelverton, E., et al., *Nuc. Acid Res.*, 9: 731 (1981); Streuli, M., et al., *Proc. Nat'l. Acad. Sci.* (U.S.., 78: 2848 (1981). The expressed proteins or polypeptides have been purified and tested and have been found to exhibit properties similar to those of native IFNs. Bacterially produced IFN's thus appear to have potential therapeutic use as antiviral and anti-tumor agents and the production of IFN's by such bacterial fermentations is expected to yield large enough quantities of IFN at a relatively low cost for clinical testing.

Native β-interferon is generally produced by superinducing human fibroblast cultures with poly-IC (polyriboinosinic acid and polyribocytidylic acid) and isolating and purifying the β-HIFN thus produced by chromatographic and electrophoretic techniques. Proteins or polypeptides which exhibit native β-interferon like properties may also be produced using recombinant DNA (r-DNA) technology by extracting poly-A-rich 12S messenger RNA from virally induced human cells, synthesizing double-stranded c-DNA using the m-RNA as a template, introducing the c-DNA into an appropriate cloning vector, transforming suitable microorganisms with the vector, harvesting the bacteria and extracting the β-HIFN therefrom. European Pat. application Nos. 28033, published May 6, 1981; 321134, published Jul. 15, 1981; 34307 published Aug. 26, 1981; Belgian Patent No. 837397, issued Jun. 1, 1981 describe various currently used methods for the production of β-interferon employing r-DNA techniques.

However, interferon samples for use in clinical studies must be of relatively high purity and substantially uncontaminated with toxic host cell constituents, cell debris and other extraneous chemicals introduced during the extraction and purification steps. There are several methods currently available for the preparation, recovery and purification of bacterially produced IFNs.

U.S. Pat. No. 4,315,852, "Extraction of Interferon from Bacteria," issued to Leibowitz et al., describes and claims a method for the acid extraction of leukocyte interferon from bacterial cells and neutralization of the extractant to obtain the interferon.

Derynck et al., *Nature*, 287: 193 (1980) teach lysing transformed *E. coli* cells using a solution containing 5 M urea, 1% SDS, and 1% 2-mercaptoethanol. The lysate which was purified by chromatography, exhibited interferon activity.

Scandella and Kornberg, *Biochemistry*, 10: 4447 (1971) describe the preparation of a phospholipase from *E. coli* by solubilizing the cell membranes with SDS and precipitating the solubilized protein with 1-butanol.

U.S. Pat. No. 4,343,735, "Process For The Purification Of Interferon," issued to Menge, et al., teaches a process for the purification of interferon by partitioning it in an aqueous multi-phase system in the presence of ion exchangers which are soluble in the system and are derivatives of polyethers.

U. S. Pat. No. 4,343,736, "Process For Recovering Interferon," issued to Uemura et al., discloses a method for recovering interferon by absorption on water insolubilized heparin and then eluting the interferon with an aqueous solution of an inorganic salt and chondroitin sulfate.

A major problem with the above methods of purification and recovery of IFN is that the protein is not produced in a pure enough form and in large enough quantities for clinical and therapeutic purposes, and further, that the resulting IFN preparations, especially those that are produced by r-DNA techniques, have residual toxic amounts of chemicals, such as sodium dodecyl sulfate (SDS) and other surfactants or precipitants used in the extraction and purification steps. Thus these preparations are not acceptable for clinical studies designed to determine the extent of the therapeutic use and applications of IFN. It would be desirable, therefore, to have available a process for the recovery of β-interferon in large enough quantities and without toxic levels of SDS for clinical and therapeutic applications.

Accordingly, it is an object of the present invention to provide a pharmaceutically acceptable sample of microbially produced β-interferon which is of relatively high purity.

Another object of the present invention is to provide pharamaceutically acceptable samples of β-interferon in sufficiently large quantities for clinical and therapeutic applications.

Yet another object of the instant invention is to provide β-interferon preparations that are substantially free of SDS without loss of their biological activity, or at levels that are therapeutically acceptable.

A further object of this invention is to provide β-interferon samples wherein the level of SDS is less than about 10 p.p.m.

Additional objects, advantages and novel features of the invention will be set forth in part in the description which follows, and in part will become apparent to those skilled in the art upon examination of the following or may be learned by practice of the invention. The objects and advantages may be attained by means of the instrumentalities and combinations particularly pointed out in the appended claims.

SUMMARY OF THE INVENTION

As used herein, β-HIFN means human β-interferon or β-interferon-like polypeptides produced by r-DNA techniques and whose amino acid sequence is the same, similar or substantially homologous to native β-interferon, both the glycosylated and/or the unglycosylated protein.

To achieve the foregoing and other objects and in accordance with the purpose of the present invention, as embodied and broadly described herein, one aspect of the invention is an improved method for the production, recovery and purification of β-HIFN and comprises solubilizing the β-HIFN into an aqueous medium with a suitable solubilizing agent, extracting the solubilized β-HIFN with an aliphatic alcohol, precipitating the β-HIFN from the alcohol phase with an aqueous buffer, and diafiltering the β-HIFN at a pH of about 10.5 to 12.5, preferably at a pH of about 12, against water adjusted to a pH of about 10.5 to 12.5, preferably about 12, or against mixtures of water and aliphatic alcohols, preferably ethanol and glycerol adjusted to a pH of about 10.5 to 12.5, preferably about 12, to substantially remove SDS or to reduce its concentration to therapeutically acceptable levels. The β-HIFN sample is optionally purified by conventional methods such as chromatography prior to the diafiltration.

A preferred embodiment of the present invention comprises recovering bacterially produced β-HIFN by disruption of the bacterial cells, solubilization of the β-HIFN with a suitable solubilizing agent, extracting the solubilized β-HIFN with an aliphatic alcohol of 2-6, preferably 4-6 carbon chain length, precipitating the β-HIFN from the alcohol phase, further purifying the β-HIFN by conventional methods, preferably gel filtration chromatography, and diafiltering the β-HIFN fraction at a pH about 10.5 to 12.5, preferably at a pH of about 12, against pure water or mixtures of water and aliphatic alcohols, preferably methanol, ethanol, propanol, butanol, glycerol and the like, also adjusted to a pH of about 10.5 to 12.5, preferably about 12.

Another aspect of the present invention deals with an improved process for the recovery of β-HIFN and a therapeutic formulation thereof where the levels of SDS are less than about 10 p.p.m.

According to yet another aspect of the invention, the diafiltered β-HIFN may be stabilized against denaturation and loss of biological activity by the inclusion of a stabilizer, which includes but is not limited to proteins or carbohydrates preferably chosen from the group consisting of human serum albumin (HSA), mannitol, sorbitol, glycerol and dextrose or mixture thereof.

In a further aspect of the present invention, the β-HIFN preparation obtained from the diafiltration and stabilization steps may be lyophilized and reconstituted in an inert, non-toxic, physiologically compatible carrier medium for therapeutic and clinical applications.

Another aspect of the instant invention provides therapeutic formulations containing therapeutically effective amounts of the β-IFN for clinical use.

DETAILED DESCRIPTION OF THE INVENTION

Many of the methods used for the recovery of bacterially produced β-HIFN utilize SDS or similar surfactants for the solubilization and isolation of β-HIFN from cellular material and subsequent acid precipitation to obtain the protein. By further purification techniques carried out at or near neutral pH, the SDS levels in the final protein preparations are reduced to about 0.1% but even these residual levels have been found by us to be toxic in animal studies and thus not acceptable for therapeutic or clinical applications. We have also found that further removal of SDS by diafiltration techniques in the 4-8 pH range results in almost complete loss of β-HIFN activity due to aggregation and the precipitation of the protein. We have observed that the biological activity of β-HIFN lost during diafiltration is regained by the addition of SDS.

Figure 4:
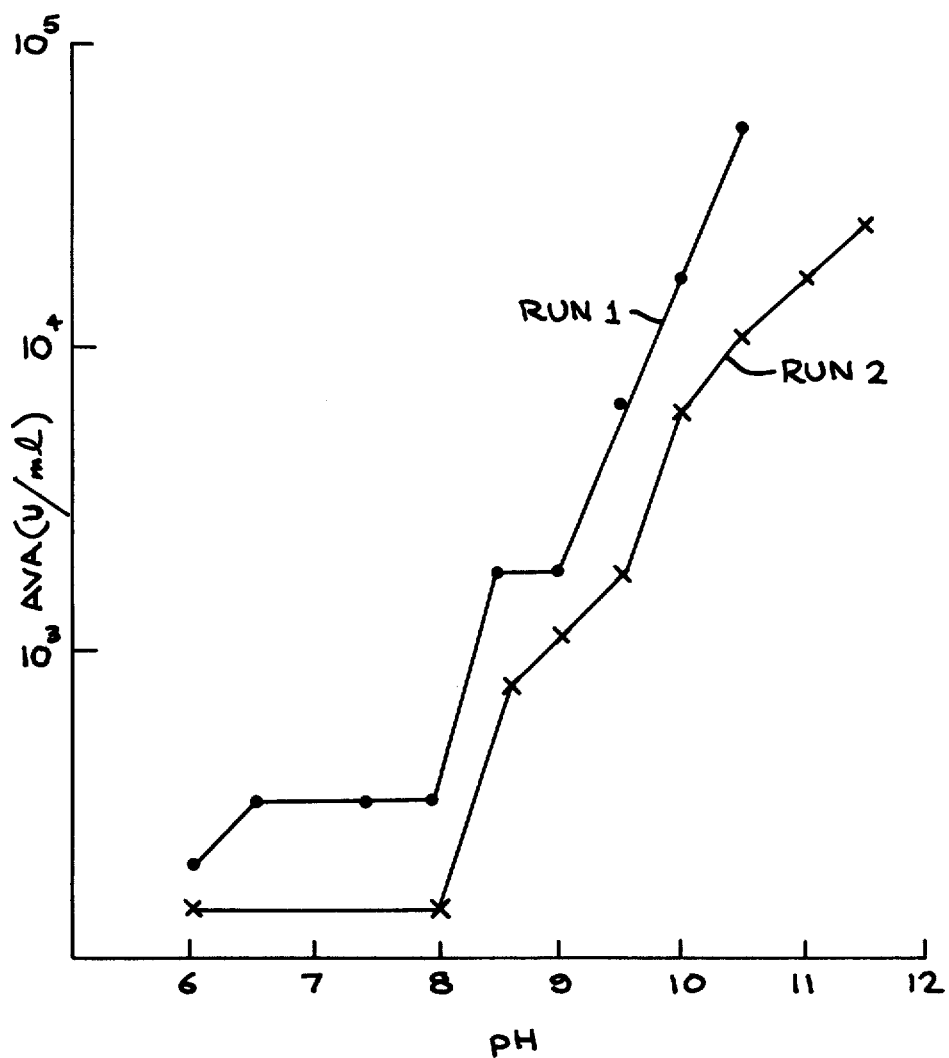
FIG. 4 is a plot of the antiviral activity of β-HIFN as a function of pH in the range of about 6-12.

For a free or unbound solute, the removal rate during diafiltration from a well mixed vessel follows first order kinetics. Since unbound SDS below its critical micelle concentration is a molecule small enough to pass unhindered through a 10,000 dalton cut-off membrane, its removal rate would be expected to follow first order kinetics and if that were the case, SDS at an initial concentration of about 1000 $\mu$g/ml should be reduced to less than 1 $\mu$g/ml after about seven volume replacements. It was found, however, that SDS removal from β-HIFN did not fit this theoretical model indicating that there were protein-SDS interactions which significantly affected the kinetics of SDS removal, and that SDS removal from this bound state in the 4-8 pH range promoted protein-protein interactions resulting in aggregation or precipitation of the protein. Higher pH ranges for SDS removal would not be expected to be desirable, as at higher pH, some proteins are known to be denatured. However, we have shown that following the removal of SDS by diafiltration at low ionic strength, increasing the pH by the addition of sodium hydroxide restores the biological activity of β-HIFN (FIG. 4). The recovery of activity is essentially complete at about pH 12.

Thus, the present invention solves the problem of β-HIFN aggregation and precipitation and loss of β-HIFN activity with the removal of SDS by initially adjusting the pH to about 10.5 to 12.5 and diafiltering against distilled water or aqueous mixtures of alcohols, using a 10,000 molecular weight cut-off ultrafiltration membrane after optionally reducing a partially purified sample of β-HIFN with dithiothreitol (DTT or mercaptoethanol or glutathione or cysteine at about 60° C. and a pH of about 8.5 to prevent aggregation of the protein. Exemplary alcohols include ethanol, butanols, glycerol, mannitol, sorbitol, dextrose and the like.

The subject invention is therefore a process for the recovery of β-HIFN (or other proteins with similar lipophilic properties) of relatively high purity containing lower than toxic levels of SDS and which can be reconstituted into therapeutically acceptable formulations in an appropriate carrier medium, and protein compositions, more specifically, β-HIFN compositions wherein SDS levels are at less than 10 p.p.m., usually in the range of 2–6 p.p.m.

For purposes of practising the present invention, bacteria are the preferred microorganism, *E. coli* being the most preferred.

One preferred embodiment of the process of the instant invention is summarized below.

FIG. 1 illustrates the details of the individual process steps of the present invention including the culture of the transformed microorganisms in an appropriate fermentation medium through the final step where the purified β-HIFN is lyophilized and may be reconstituted into therapeutic formulations. The individual process steps include:

growing the transformed bacterial hosts in an appropriate fermentation medium;

concentrating the bacteria in the fermentation medium by cross-flow filtration;

mechanically homogenizing the bacteria to disrupt the cell walls of the bacteria;

separating solid cellular material from the remainder of the homogenate by centrifugation;

solubilizing the solid cellular material by suspending it in an aqueous solution of sodium dodecyl sulfate (SDS) at a protein to SDS ratio of about 1:3;

extracting the β-HIFN from the aqueous phase with 2-butanol or 2-methyl-2-butanol or mixtures thereof by continuous cocurrent extraction;

heating the 2-butanol or 2-methyl-2-butanol phase to about 60° C. for about 10 to 20 minutes; or aging the 2-butanol phase overnight;

centrifuging the mixture and discarding the precipitated impurities;

contacting the 2-butanol or 2-methyl-2-butanol phase with an aqueous buffer and adjusting the pH of the mixture to about 5.5 to precipitate the β-HIFN;

collecting the precipitated β-HIFN by centrifugation;

solubilizing the β-HIFN with distilled water or with an aqueous solution of sodium dodecyl sulfate at a protein to SDS ratio of about 1:3;

adjusting the pH of the solution to about 9.5 and reducing the solubilized β-HIFN with dithiothreitol;

purifying the reduced β-HIFN by chromatography;

collecting the eluted fraction of the purified β-HIFN;

further purifying the β-HIFN by gel chromatography;

collecting the eluate containing the purified β-HIFN;

adjusting the pH of the eluate to about 12;

diafiltering the solution containing the β-HIFN at a pH of about 12 against pure water or $H_2O$-ethanol mixtures adjusted to a pH of about 12;

stabilizing the β-HIFN by the addition of a 0.5–10% by weight solution of dextrose and human serum albumin adjusted to a pH of about 12;

adjusting the pH of the solution down to physiological pH;

and lyophilizing the β-HIFN sample, if desired.

10 mM dithiothreitol may be optionally included in the initial solubilization step and the mixture heated to about 90° C. for about 10 minutes.

Generally, proteins are susceptible to denaturation, peptide bond hydrolysis, hydrolysis of individual amino acids, β-elimination, racemization, formation of different amino acids and similar reactions in the high alkaline pH range, but with β-HIFN, none of the degradative reactions enumerated above are detected. On the other hand, when the protein is diafiltered at a pH of about 12, the resulting β-HIFN is pure, homogeneous and exhibits high specific activity, close to that of native β-HIFN.

The transformed microorganisms are grown in a suitable growth medium, typically to an optical density (OD) of at least about 10 at 680 nm, and preferably between about 50 and 100 at 680 nm. The composition of the growth medium will depend upon the particular microorganism involved. The aqueous growth medium contains compounds that fulfill the nutritional requirements of the microorganism of choice. Growth media will typically contain assimilable sources of carbon and nitrogen, energy sources, magnesium, potassium and sodium ions, and optionally amino acids and purine and pyrimidine bases. (Review of Medical Microbiology, Lange Medical Publications, 14th Ed pp. 80–85 (1980)). Growth media for *E. coli* are well known in the art. Depending upon the particular solubilizing agent used in the invention process it may be desirable to minimize the amount of substances in the growth medium that may decrease the solubility of the solubilizing agent in water. For instance, potassium ions affect the solubility of SDS and, therefore, should be kept to a minimum when SDS is used as a solubilizing agent in the process, or removed by diafiltration following the concentration step.

Once the culture has reached the desired cell density, the cells are optionally killed or inactivated by heating or adding to the medium a cytotoxic agent such as chloroform or toluene that may be removed easily after the cells have been killed. The cells are thereafter optionally concentrated to about 20 to 150 mg/ml, preferably 80 to 100 mg/ml (OD 40 to 300, preferably 160 to 200 at 680 nm) by cross-flow filtration, centrifugation, or other conventional methods.

Following the concentration step, the cell membranes of the microorganisms are disrupted to facilitate the solubilization of the particulate matter in the concentrate. β-HIFN assays for biological activity indicate that much of the interferon is associated with (i.e., contained in or bound to) the cell membrane. Accordingly, disruption of the cell membrane enhances the contact of the solubilizing agent with the membranes and thus increases the rate at which the interferon associated with the membrane goes into solution. Conventional cell disruption techniques such as homogenization, sonication, or pressure cycling may be used in this step of the process. A preferred method is using a bead mill or a pressure homogenizer. Either before or after the disruption, the pH of the liquid phase of the concentrate or disruptate, as the case may be, is adjusted if necessary, to a level that facilitates dissolution of the solubilizing agent and the particulate matter in the concentrate/disruptate. The pH may be so adjusted by adding suitable buffers or with NaOH. In most instances a pH in the range of about 7 to about 8 is preferred.

After the cells have been disrupted the particulate matter can be separated from the liquid phase of the disruptate and resuspended in an aqueous medium buffered to the optimal pH for solubilization. The protein concentration of the cell suspension after solubilization is in the range of about 2 to about 15 mg/ml, preferably 6 to 8 mg/ml.

The solubilization of the particulate cellular material, including the β-IFN, can be carried out concurrently with the disruption or sequentially following the disruption. It is preferably carried out as a separate step following the disruption. The solubilization is preferably carried to completion—that is, substantially all of the particulate matter (e.g., protein, lipids, nucleic acids, phospholipids) in the disruptate is dissolved into the aqueous medium. Substantially complete dissolution of the particulate matter is achieved by adding an appropriate solubilizing agent to the aqueous suspension. Surfactants (detergents) that have a suitable hydrophobic-hydrophilic balance to solubilize β-HIFN and which form a complex with β-HIFN that can be extracted into the organic phase can be used in the invention. Strong natural or synthetic anionic surfactants such as alkali metal salts of fatty acids and alkali metal alkyl sulfates may be used. Such agents will usually contain 10 to 14 carbon atoms. Sodium dodecyl sulfate (SDS) and sodium laurate are particularly preferred solubilizing agents. Examples of other solubilizing agents that can be used in the process include but are not limited to sodium dodecyl sulfonate, sodium decyl sulfate, sodium tetradecyl sulfate, sodium tridecyl sulfonate, sodium myristate, sodium caproylate, sodium dodecyl N-sarcosinate, and sodium tetradecyl N-sarcosinate.

The amount of solubilizing agent used in the solubilization depends upon the particular agent and the amount of protein to be solubilized. In most instances, solubilizing agent to protein weight ratios in the range of about 1:1 to 10:1 are sufficient. When SDS is used, an SDS to protein ratio of about 1:1 to about 5:1, preferably about 3:1, is used. Temperatures in the range of 15° C. to 60° C. are normally used in the solubilization. Mixing may be employed to enhance contact between the solution and particulate matter and thus decrease the time it takes to dissolve the cellular matter. The solubilization is considered complete when the solution is substantially clear. ODs of about 4.0 to 8.0 at 280 nm are characteristic of the end point of the solubilization process.

Following the solubilization, the ionic strength of the solution is adjusted, if necessary, to a level at which the solution and organic extractant are substantially immiscible. The ionic strength is in the range of about 0.05 to 0.15. Inorganic salts, including NaCl and the like are added to the solution for this purpose. Such ionic strengths enable phase separation after the extraction. The extractants used in the process are alcohols such as 2-butanol, 2-methyl-2-butanol, or mixtures thereof. The mixtures preferably contain less than about 50% by volume of 2-methyl-2-butanol. 2-butanol is the preferred extractant. The ability of these alcohols to extract human β-IFN- from the solubilizate is specific. The extractant is normally combined with the aqueous solution of β-HIFN in volume ratios in the range of about 0.8:1 to about 3:1, preferably about 1:1 (extractant:aqueous solution). The extraction can be carried out using conventional batch or continuous liquid-liquid extraction techniques and equipment. The extraction is normally carried out at about 20° C. to 100° C. and involves contact times in the range of about one minute to one hour. The optimum contact time depends upon the particular solubilizing agent and extractant combination. When SDS is used, shorter times in the above range can be used. When sodium laurate is used, longer times in the range must be used. The pH of the extraction mixture ranges between about 6 and 9, with a pH of about 7.5 being preferred when SDS is used and a pH of about 8.5 when sodium laurate is used.

Figure 1A:
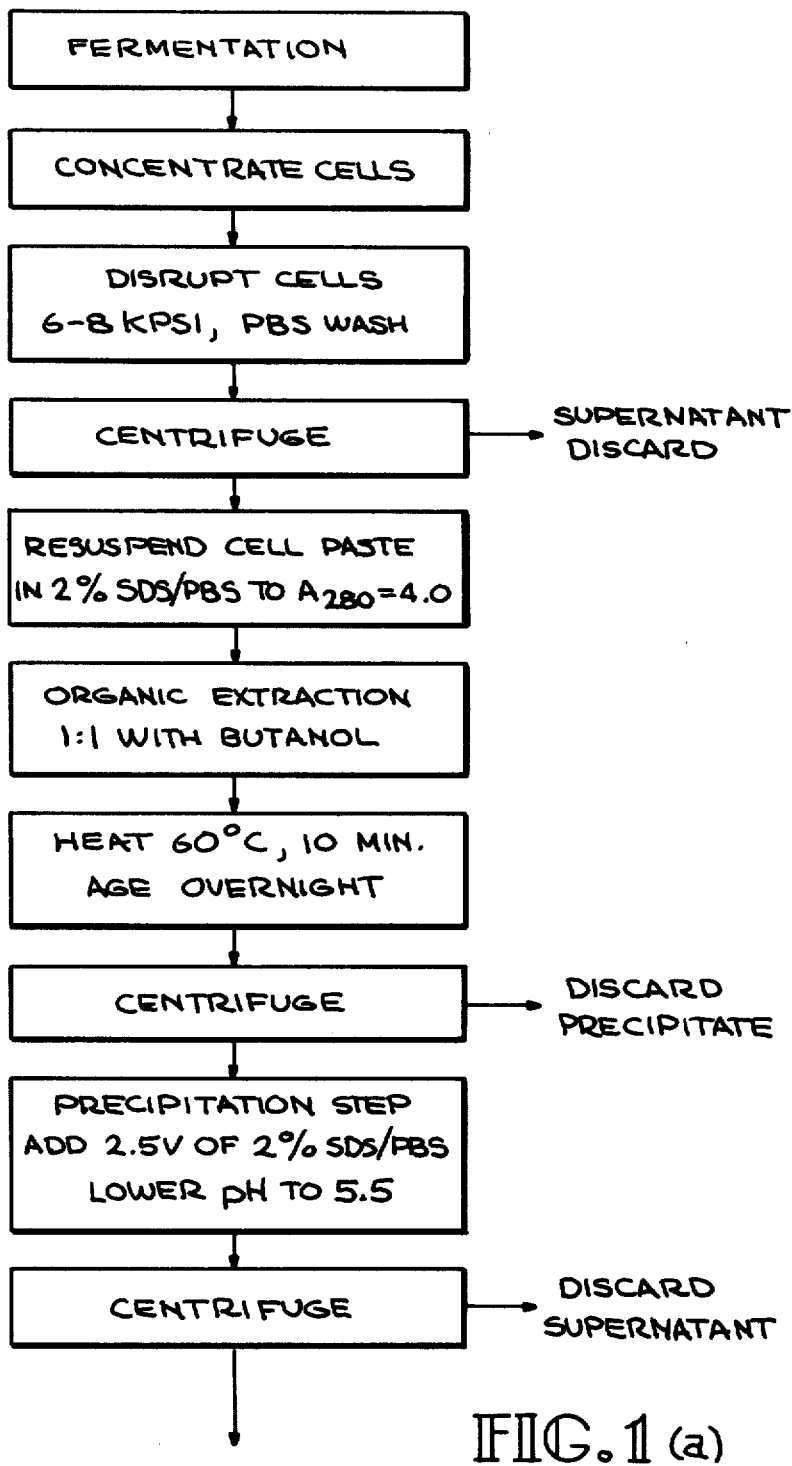
FIG. 1 illustrates a flow chart of the process steps of the present invention.
Figure 1:
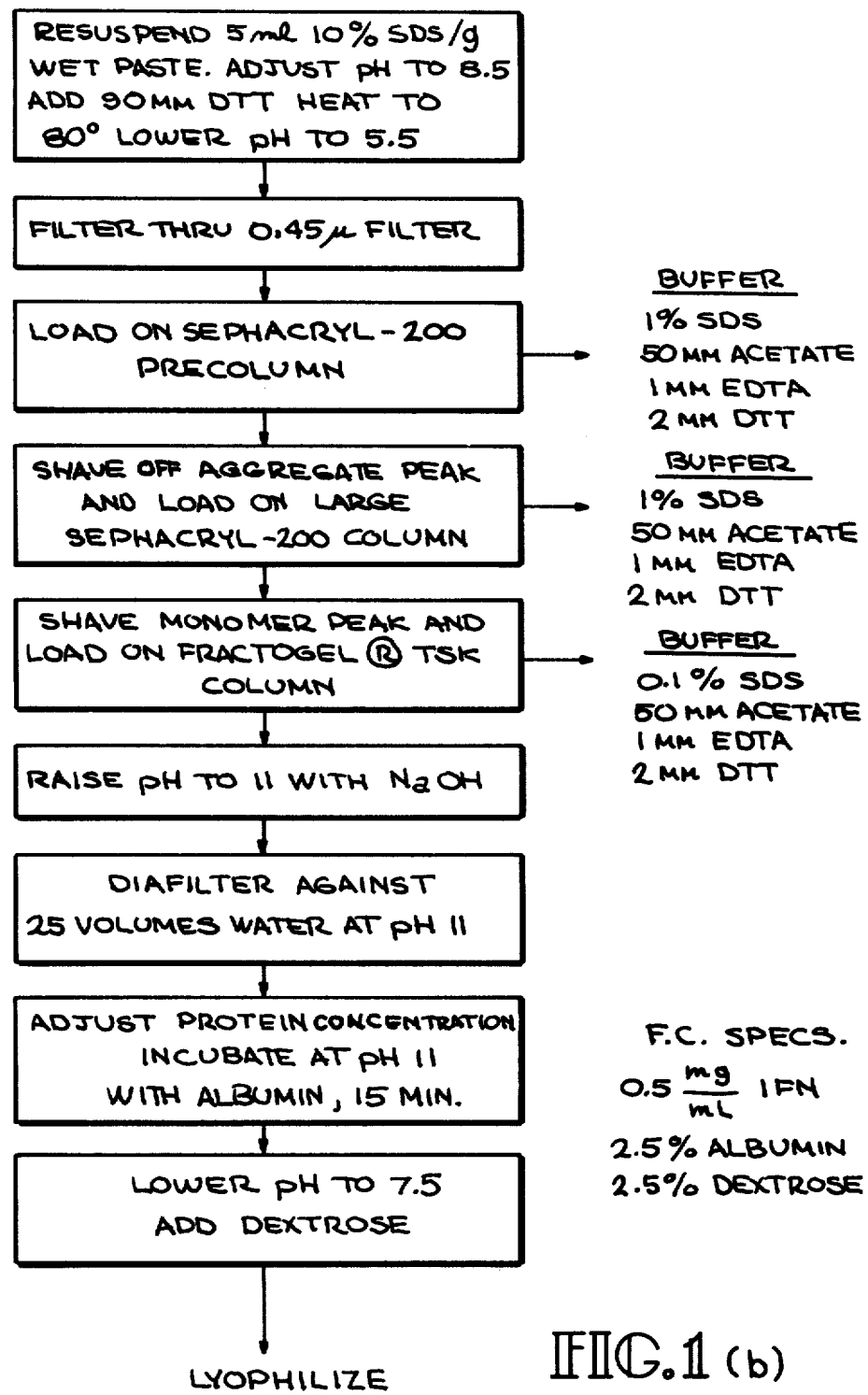
Figure 2:
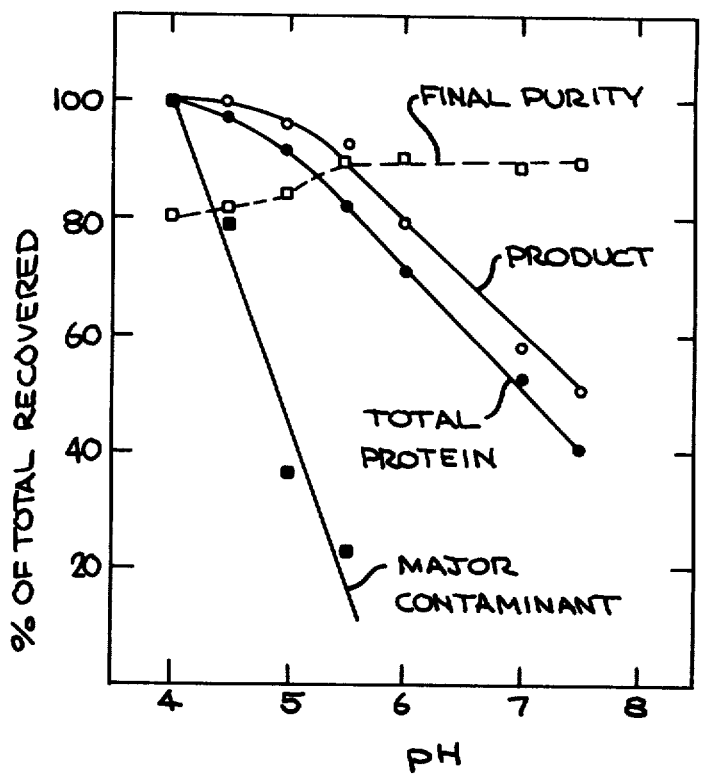
FIG. 2 shows a graph plotting percentage of the total recovery of β-HIFN and purity of the product during the precipitation step, as a function of pH in the range of about 4-8.

Upon completion of the extraction, the aqueous phase and extractant phase are separated and the β-HIFN is isolated from the extractant phase. The particular isolation procedure used depends upon the solubilizing agent involved and the desired degree of purity of the final product. Various isolation techniques such as precipitation, molecular sieve chromatography, affinity chromatography, and electrophoresis are employed. In instances in which SDS is used, the β-HIFN together with other proteins are precipitated from the extractant by mixing the extractant solution with aqueous buffer at volume ratios of about 2.0:1 to about 5:1, preferably about 3:1 and reducing the pH, typically to the range of about 5 to 7. The recovery of β-HIFN in the range of the pH 4 to 8, as shown in FIG. 2, shows a downward trend in the recovery of the protein with increasing pH, with an appreciable loss in the recovery of greater than 60% at a pH of about 8. Separation of the precipitate from the supernatant and evaporation of residual extractant from the precipitate provide a product that is greater than about 90% pure protein provided that the pH of the precipitation step is greater than 5.5. This product also contains minor amounts of nucleic acids (<1% to 2% by weight) and SDS (<1% w/v). After further purification by methods known in the art including but not limited to chromatography, SDS is removed by diafiltration at a pH of about 10.5 to 12.5, preferably about 12. The second purification step is optional and is not required for SDS removal by diafiltration. When sodium laurate is used as a solubilizing agent it precipitates from the extractant together with the protein on lowering the pH. Sodium laurate is extracted from the protein using organic solvents such as acetone, methanol and the like. Prior to diafiltration, β-HIFN may be optionally reduced with appropriate reducing agents. Mercaptoethanol, glutathione, cysteine and dithiothreitol (DTT) are normally employed, DTT being the most preferred.

The β-HIFN thus isolated can be lyophilized or stored in solution pending use. Nontoxic, nontherapeutic, nonimmunogenic stabilizers may be optionally added to the β-HIFN. Diluents that can be used in the solutions for thereapeutic or clinical administrations are selected from aqueous based vehicles commonly used to formulate pharmaceuticals for animal or human administration. The diluent should, of course, not affect the biological activity of the β-HIFN. Examples of such diluents are distilled water, physiological saline, Ringer's solution, dextrose solution, and Hank's solution. The same diluents can be used to reconstitute lyophilized β-HIFN.

The process of the present invention is further described by the following examples. These examples are provided for purposes of illustration only and are not intended to limit the invention in any manner.

EXAMPLE 1

Cell Production and Harvest

Human β-HIFN was recovered from *E. coli* that had been transformed to produce β-HIFN. The *E. coli* were grown in the following growth medium to a cell density (OD) of 10–11 at 680 nm (dry wt 10 g/l).

| Ingredient | Concentration |
|---|---|
| $NH_4Cl$ | 20 mM |
| $K_2SO_4$ | 16.1 mM |
| $KH_2PO_4$ | 7.8 mM |
| $Na_2HPO_4$ | 12.2 mM |
| $MgSO_4 \cdot 7H_2O$ | 3 mM |
| $Na_3$ citrate $2H_2O$ | 1.5 mM |
| $MnSO_4 \cdot 4H_2O$ | 30 µM |
| $ZnSO_4 \cdot 7H_2O$ | 30 µM |
| $CuSO_4 \cdot 5H_2O$ | 3 µM |
| L-tryptophan | 70 mg/l |
| $FeSO_4 \cdot 7H_2O$ | 72 µM |
| thiamine HCl | 20 mg/l |
| tetracycline | 10 mg/l |
| glucose | 40 g/l | pH was controlled with $NH_4OH$.

The bacteria were then harvested and concentrated in a hollow-fiber cross-flow filtration system, using microporous polypropylene fiber system with an I.D. of about 0.3 mm and a recirculation rate of about 3.5 gpm/cartridge.

EXAMPLE 2

Cell Disruption

The cells, at a final concentration of 9–10% (w/v) were mechanically disrupted by means of a Manton-Gaulin type homogenizer (Gray, P.P., et al., IV IFS: Ferment. Tech. Today, 347–351 (1972)), fitted with a special valve. A single pass at 6-10,000 psig pressure drop yielded greater than 90% cell disruption. The cells were subjected to three passes to obtain maximum disruption without losing β-HIFN activity and to shear nucieic acids to reduce viscosity.

EXAMPLE 3

Centrifugation Of Homogenate

The homogenized cell material was diluted with 1:1 (v/v) with phosphate buffered saline (PBS) at a pH of about 7.4 to give a final volume of two liters. This material was continuously centrifuged at 12,000×g at a flow rate of about 50 ml/min. The solid material was separated from the supernatant and resuspended in four liters of PBS containing two percent by weight of SDS. This suspension was stirred at room temperature for 15 min. after which there was no visible suspended material. The solution was then extracted with 2-butanol at a 1:1 volume ratio of 2-butanol to solution. Tne extraction was carried out in a liquid-liquid phase separator using a combined flow rate of about 200 ml/min. The organic phase was then separated and evaporated to dryness to yield 21.3 g of protein. This was resuspended in distilled water at a 1:10 volume ratio.

The recovered product was assayed for β-HIFN using an assay based on protection against viral cytopathic effect (CPE). The assay was made in microtiter plates. Fifty µl of minimum essential medium were charged into each well and 1:3 volume dilutions were made serially into the following wells. Virus (vesicular stomatitis), cell (human fibroblast line GM-2504), and reference β-HIFN controls were included on each plate. The reference β-HIFN was 100 units per ml. The plates were then irradiated with UV light for 10 min. After irradiation 100 µl of the cell suspension (1.2×10⁵ cells/ml) was added to each well and the trays were incubated for 18–24 hr. A virus solution at one plaque-forming unit per cell was added to each well except to the cell control. The trays were then incubated until the virus control showed 100% CPE. This normally occurred 18–24 hr after adding the virus solution. Assay results were interpreted in relation to the location of the 50% CPE well of the reference β-HIFN control. From this point the titer of interferon for all samples on the plate were determined. The activity of the recovered product was determined to be $2.9 \times 10^6$ IU/mg.

EXAMPLE 4

Extraction of β-HIFN

A 10 l tank was harvested (9.8kg) and concentrated to 2.2 liters by cross-flow filtration. The slurry was frozen and stored for 34 days and then thawed.

The thawed concentrate was disrupted by three passes at $7 \times 10^4$ kPa in a Manton-Gaulin homogenizer. The disruptate was collected and made up to 4 liters with a solution of sodium laurate to give a final concentration of 1% w/v laurate. The pH was adjusted to 8.5 with 10% NaOH. The solution was contacted with a mixture of 50 vol. % 2-butanol and 50 vol. % 2-methyl-2-butanol in a static mixer. The emulsion was pumped into a holding tank and agitated to give a contacting time of 15 minutes. This emulsion was separated as described in Example 3 and the β-HIFN recovered in the organic phase. The activity recovered was 16% of the initial value with a specific activity (determined as in Example 3) of $3.7 \times 10^5$ IU/mg protein.

EXAMPLE 5

Acid Precipitation of β-HIFN

The process of Example 4 was repeated except that after extraction and separation of the aqueous and organic phases the organic phase was mixed with PBS or 10 mM phosphate buffer at a pH of about 7.4 at a volume ratio of 3:1. The pH of the mixture was lowered to about 5.5 by the addition of glacial acetic acid. The resulting precipitate was separated by centrifugation at 10000–17000 ×g for 15 min. and the pellet was redissolved in 10% w/v SDS.

The precipitate was applied to a molecular sieve column with a Sephacryl S-200 ® Superfine matrix. The column was equilibrated with 50 mM sodium acetate buffer at pH 5.5 containing 2 mM dithiothreitol and 1.0% SDS (w/v). The column was developed with the same buffer at a flow rate of 5 ml per cm² per hour. Protein profile was monitored at 280 nm with a UV spectrophotometer. Fractions collected were assayed for protein content by methods known in the art. Interferon concentration was determined by the CPE assay as described in Example 3. Degree of interferon purity was determined by SDS polyacrylamide gel electrophoresis (PAGE). Fractions containing highest interferon activities were pooled and the specific activity of the pooled interferon preparation was determined to be $1-2 \times 10^7$ IU/mg protein.

EXAMPLE 6

Final Chromatography

Figure 3:
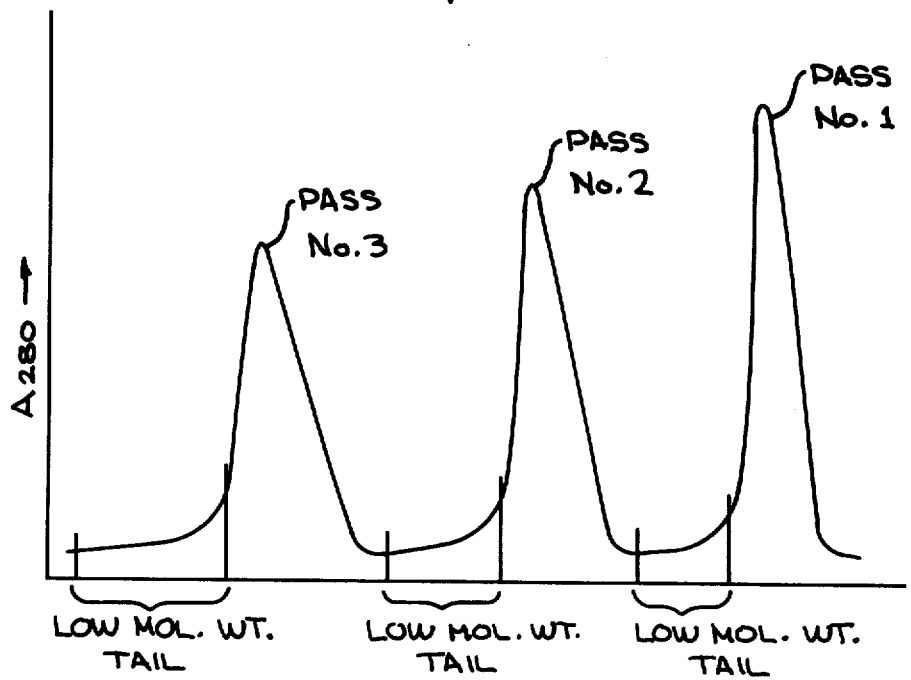
FIG. 3 is a representation of a chromatographic chart illustrating the homogeneity of the β-HIFN fraction eluted after three passes through a vinyl polymer gel (Fractogel) ® column.

The process of Example 5 was continued by concentrating the pool from the Sephacryl-200 step ten fold using a 10,000 nm wt. (nominal molecular weight) cut-off filter and then applying the material to a fine vinyl polymer gel (Fractogel-TSK HW55)® column. This column was equilibrated with 50 mM sodium acetate buffer at pH 5.5 containing 2 mM dithiothreitol and 0.1% SDS (w/v). The column was developed with the same buffer at a flow rate of 15.6 ml/cm$^2$/hr. The protein profile was monitored at 280 nm with a spectrophotometer and the protein peak was recycled three times prior to being collected and fractions were assayed for protein activity and purity by SDS-PAGE. FIG. 3 depicts the eluate peaks after the first, second and third passes as monitored by the protein ($\beta$-HIFN) concentration plotted as O.D. vs. eluate fractions exhibiting protein absorption at 280 n.m. The peak area after each pass remained substantially the same indicating that there was no protein loss and that the preparation remained substantially homogeneous after three passes. Fractions containing the highest interferon assay by the cytopathic effect assay were pooled. Specific activity of the pool was in the range of 1-2×10$^7$ IU/mg protein.

EXAMPLE 7

Removal Of Residual Reagents

The pH of the pool collected in Example 6 above was raised to pH 12 and placed in a diafiltration device. This protein was reduced by treatment with IOmM dithiothreitol (DTT) at pH 8.5 prior to raising the pH of the pool to 12 with 2.5 M sodium hydroxide. Reduction with DTT was optional and may be omitted if desired.

Diafiltration was carried out at 1 mg/ml protein using a hollow fiber ultrafiltration cell equipped with a 1 sq. ft. surface area (10,000 dalton cut off) cartridge. The pool was diafiltered against 20 volume exchanges of water with the pH adjusted to 12 with 2.5 M sodium hydroxide. Sodium dodecyl sulfate levels were monitored and residual levels were found to be less than 10 p.p.m. Residual DTT, EDTA and other low molecular weight species were undetectable. The specific activity of the protein following diafiltration was unchanged from that prior to diafiltration. As shown in FIG. 4, the antiviral activity of $\beta$-HIFN following diafiltration was not lost even at a pH of 12.

EXAMPEL 8

Formulation With Human Serum Albumin/Dextrose

The diafiltered interferon ($\beta$-HIFN) from Example 7 was diluted to 0.25 mg/ml and incubated with pharmaceutical grade human serum albumin (final concentration 1.25% v/v) for 15 minutes at pH 12. The pH of the solution was then lowered to 7.5±0.3 with dilute hydrochloric acid and pharmaceutical grade dextrose was added to a final concentration of 1.25%. The pool was then sterile filtered through an absolute 0.2 $\mu$m filter. Specific activity of the formulated material was 1-2×10$^7$ IU/mg interferon.

EXAMPLE 9

Lyophilization And Reconstitution

The sterile formulated interferon pool was filled in 4 ml aliquots and lyophilized using the following cycle.

1. Product at −35° C., ≦100 millitorr for at least 1 hour.
2. Product at −20° C., ≦100 millitorr for at least 1 hour.
3. Product at +25° C., ≦100 millitorr for at least 4 hour.

The vials were then sealed under 10″ Hg vacuum.

The product was reconstituted in distilled water for injection to either 0.5 mg IFN/ml or 1 mg IFN/ml. Specific activity of the product corresponded to 0.9-1×10$^7$ IU/mg $\beta$-HIFN.

The process and compositions of the present invention as described herein yield a $\beta$-HIFN preparation which is of relatively high purity, with residual SDS levels of less than about 10 p.p.m. and which may be formulated into therapeutically acceptable preparations in a non-toxic, inert, physiologically compatible carrier medium for clinical and therapeutic uses. The principal advantage of the instant invention lies in the reduction of SDS levels in the $\beta$-HIFN preparation to about 2-20 p.p.m., usually less than about 10 p.p.m., and preferably to about 2-6 p.p.m., which are therapeutically acceptable. Although the preferred embodiment described relates to $\beta$-HIFN specifically, the diafiltration method of the instant invention can be used to purify other proteins with similar lipophilic characteristics as $\beta$-HIFN.

The foregoing description of the preferred embodiments of the instant invention have been presented for purposes of illustration and description. It is not intended to be exhaustive or to limit the invention to the precise form disclosed, and obviously many modifications and variations are possible in the light of the above teaching. The particular embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. In a process for the recovery of a lipophilic protein from a microorganism transformed to produce said protein wherein the steps comprise:

solubilizing said protein in an aqueous medium with an appropriate solubilizing agent;

extracting said solubilized protein from the aqueous medium with an aliphatic alcohol selected from the group consisting of 2-butanol, 2-methyl-2-butanol and mixtures thereof;

precipitating said protein from the alcohol phase; the improvement which comprises purifying said precipitated protein by diafiltration at a pH of about 10.5 to 12.5.

2. A process according to claim 1, wherein said lipophilic protein is $\beta$-HIFN.

3. A process according to claim 2, wherein said solubilizing agent is an anionic surfactant.

4. A process according to claim 3, wherein said surfactant is sodium dodecyl sulfate or sodium laurate.

5. A process according to claim 4, wherein the weight ratio of said surfactant to said $\beta$-HIFN is in the ratio of about 1:1 to about 5:1.

6. A process according to claim 5, wherein said ratio is about 3:1.

7. In a process for the recovery of unglycosylated β-HIFN from a microorganism transformed to produce said β-HIFN wherein the steps comprise:
 a. disrupting the cell wall of said microorganism;
 b. solubilizing said β-HIFN in the disruptate into an aqueous medium with solubilizing agent;
 c. extracting said solubilized β-HIFN from the aqueous medium with an aliphatic alcohol selected from the group consisting of 2-butanol, 2-methyl-2-butanol and mixtures thereof; and
 d. isolating and purifying said β-HIFN; the improvement which comprises the additional steps of:
 e. adjusting the pH of a solution containing the purified β-HIFN to about 10.5 to 12.5; and
 f. diafiltering said β-HIFN solution at a pH of about 10.5 to 12.5.

8. A process according to claim 7, including reducing said β-HIFN prior to step (e).

9. A process according to claim 8, wherein said β-HIFN is reduced with dithiothreitol or mercaptoethanol or glutathione or cysteine.

10. A process according to claim 7, wherein said β-HIFN solution in step (f) is diafiltered against distilled water adjusted to a pH of about 10.5 to 12.5.

11. A process according to claim 7, wherein said β-HIFN solution in step (f) is diafiltered against a 10% aqueous solution of ethanol adjusted to a pH of about 10.5 to 12.5.

12. A process according to claim 7, wherein said β-HIFN solution in step (f) is diafiltered against a 10% aqueous solution of a polyhydric alconol selected from a group consisting of a glycerol, mannitol, sorbitol and dextrose, adjusted to a pH of about 12.

13. A process according to claim 7, wherein said microorganism is a bacterium.

14. A process according to claim 13, wherein said bacterium is E. coli.

15. A process according to claims 7 or 14, wherein said microorganism is contained in a fermentation medium and is concentrated prior to step (a).

16. A process according to claims 7 or 15, wherein said solubilizing agent is an anionic surfactant.

17. A process according to claim 7 or 16, wherein said solubilizing agent is an alkali metal, alkyl sulfate or an alkali metal salt of a fatty acd of 10 to 14 carbon chain length.

18. A process according to claim 17, wherein said solubilizing agent is sodium dodecyl sulfate or sodium laurate.

19. A process according to claim 18, wherein said solubilizing agent is sodium dodecyl sulfate and the weight ratio of said sodium dodecyl sulfate to β-HIFN is in the range of about 1:1 to about 5:1.

20. A process according to claim 19, wherein said weight ratio is about 3:1.

21. A process according to claim 7, wherein said alcohol is 2-butanol.

22. A process according to claim 7, wherein said isolation in step (d) includes the steps of:
 contacting the alcohol extract with an aqueous buffer;
 precipitating the β-HIFN from the mixture by lowering the pH; and
 separating the precipitated β-HIFN from the supernatant.

23. A process according to claim 22, wherein the pH of the solution is lowered to about 5 to 7.

24. A process according to claims 7, 8 or 22, including adding a β-HIFN stabilizer adjusted to a pH of about 12.

25. A process according to claim 24, wherein said stabilizer is human serum albumin.

26. A process according to claim 24, wherein said stabilizer is dextrose.

27. A process according to claim 24, wherein said stabilizer is a mixture of human serum albumin and dextrose.

28. A process according to claim 25, wherein said human serum albumin is in the concentration range of about 0.5 to 10 (w/v) percent.

29. In a process for the recovery of β-HIFN from transformed E. coli bacteria comprising concentrating said bacteria, disrupting the cell wall of said bacteria, solubilizing said β-HIFN with SDS, extracting said β-HIFN with 2-butanol and precipitating said β-HIFN by mixing said butanol phase with an aqueous mixture, the improvement comprising:
 dissolving the precipitated β-HIFN in an appropriate buffer at a pH of about 9;
 reducing said β-HIFN with dithiothreitol;
 diafiltering the β-HIFN solution against water at a pH of about 10.5 to 12.5 or against a 10% (v/v) ethanol at a pH of about 10.5 to 12.5;
 adding to said β-HIFN a solution of human serum albumin and dextrose adjusted to a pH of about 10.5 to 12.5; and
 lowering the pH of the resulting β-HIFN solution to about 7 to 7.5.

30. The improvement according to claim 29, wherein said diafiltration is carried out at a pH of about 12.

31. The improvement according to claim 29 or including lyophilizing said β-HIFN.

32. In a process for the production of an unglycosylated β-HIFN from E. coli genetically transformed to produce said β-HIFN and grown in an appropriate fermentation medium wherein the steps comprise:
 (a) concentrating the bacteria in the fermentation medium by cross-flow filtration;
 (b) mechanically homogenizing the bacteria to disrupt the cell walls of the bacteria;
 (c) separating solid cellular material from the remainder of the homogenate by centrifugation;
 (d) solubilizing the solid cellular material by suspending it in an aqueous solution of sodium sulfate at a SDS to protein ratio of about 3:1;
 (e) extracting the β-HIFN from the aqueous phase with 2-butanol by continuous cocurrent extraction;
 (f) aging the 2-butanol phase overnight;
 (g) heating the 2-butanol phase to about 60° C. for about 10 to 20 minutes;
 (h) contacting the 2-butanol phase with an aqueous buffer and adjusting the pH of the mixture to aobut 5.5 to precipitate the β-HIFN;
 (i) collecting the precipitated β-HIFN by centrifugation;
 (j) solubilizing the β-HIFN with an aqueous solution of sodium dodecyl sulfate at a SDS to protein ratio of about 3:1;
 (k) reducing said solubilized β-HIFN with dithiothreitol;
 (l) purifying the reduced β-HIFN by chromatography;
 (m) collecting the eluted fraction of the purified β-HIFN;

(n) concentrating the purified β-HIFN to a concentration of about 20 mg protein/ml;
(o) further purifying the β-HIFN by gel chromatography; and
(p) collecting and dissolving the fraction eluate containing the purified β-HIFN in an aqueous buffer;
the improvement which comprises the steps of:
(q) adjusting the pH of the β-HIFN solution to about 12;
(r) diafiltering the solution containing the β-HIFN at a pH of about 12 against pure water or a $H_2O$-ethanol mixture adjusted to a pH of about 12;
(s) stabilizing the β-HIFN by the addition of a 0.5-10% by weight solution of dextrose and human serum albumin adjusted to a pH of about 12; and
(t) lowering the pH of the resulting solution to physiological pH.

* * * * *